United States Patent
Chesnin

(10) Patent No.: US 9,314,586 B2
(45) Date of Patent: Apr. 19, 2016

(54) TRIPLE LUMEN CATHETER

(75) Inventor: Kenneth J. Chesnin, Philadelphia, PA (US)

(73) Assignee: Medical Components, Inc., Harleysville, PA (US)

(*) Notice: Subject to any disclaimer, the term of this patent is extended or adjusted under 35 U.S.C. 154(b) by 1124 days.

(21) Appl. No.: 12/411,813

(22) Filed: Mar. 26, 2009

(65) Prior Publication Data
US 2009/0247868 A1  Oct. 1, 2009

Related U.S. Application Data

(60) Provisional application No. 61/039,655, filed on Mar. 26, 2008.

(51) Int. Cl.
*A61M 25/00* (2006.01)

(52) U.S. Cl.
CPC ....... *A61M 25/0032* (2013.01); *A61M 25/0026* (2013.01); *A61M 25/0023* (2013.01); *A61M 2025/0035* (2013.01); *A61M 2025/0037* (2013.01)

(58) Field of Classification Search
CPC ............ A61M 2025/0035; A61M 2025/0037; A61M 25/0023; A61M 25/0026; A61M 25/0032
USPC ..................... 604/523, 43, 164, 264; 600/435
See application file for complete search history.

(56) References Cited

U.S. PATENT DOCUMENTS

| 5,195,962 A | 3/1993 | Martin et al. |
|---|---|---|
| 5,378,230 A | 1/1995 | Mahurkar |
| 5,395,316 A | 3/1995 | Martin |
| 5,451,206 A | 9/1995 | Young |
| 5,480,392 A | 1/1996 | Mous |
| 5,556,390 A | 9/1996 | Hicks |
| 5,749,835 A | 5/1998 | Glantz |

(Continued)

FOREIGN PATENT DOCUMENTS

WO  WO98/24501  6/1998

OTHER PUBLICATIONS

Pina C. Sanelli, Monica Deshmukh, Igor Ougorets, Rachael Caiati, Linda A. Heier; Safety and Feasibility of Using a Central Venous Catheter for Rapid Contrast Injection Rates, American Journal of Roentgenology, Dec. 2004; pp. 1829 through 1834.

(Continued)

*Primary Examiner* — Imani Hayman
(74) *Attorney, Agent, or Firm* — Buchanan, Ingersoll & Rooney PC

(57) ABSTRACT

A multi-lumen catheter comprising a longitudinally extending elongated body portion, with at least two septa extending longitudinally through the entire body portion, and defining a central lumen and two side lumens. The central lumen is oblong shape in cross section and positioned between the side lumens. The septa forming the central lumen are configured to flex outwards when the central lumen is under pressure, whereby a cross sectional area of the central lumen resultantly increases to increase flow capacity through the central lumen. In some embodiments, the central lumen has a defining inner surface such that a radius of curvature of the central lumen inner surface is, in all locations, equal to or greater than a radius of curvature of an outer surface of a guide wire used for insertion of the multi-lumen catheter. The septa are each configured to fail under pressure before failure of the outer wall.

16 Claims, 3 Drawing Sheets

(56) References Cited

U.S. PATENT DOCUMENTS

| | | | |
|---|---|---|---|
| 5,947,940 A | 9/1999 | Beisel | |
| 6,544,251 B1 | 4/2003 | Crawford | |
| 2005/0261663 A1 | 11/2005 | Patterson et al. | |
| 2009/0054874 A1* | 2/2009 | Barron et al. | 604/524 |

OTHER PUBLICATIONS

Douglas Coyle, MD, Daniel Bloomgarden, MD, PhD, Robert Beres, MD, Shirish Patel, MD, Shekhar Sane, MD, and Emil Hurst, MD; Power Injection of Contrast Media via Peripherally Inserted Central Catheters for CT; J Vasc Interv Radiol 2004; 15:809-814.

International Search Report for PCT/US2009/038414.
International Preliminary Report on Patentability and Written Opinion; International Application No. PCT/US2009/038414; International Filing Date Mar. 26, 2009; 6 pages.
International Application No. PCT/US2009/038414; International Search Report, mailed May 29, 2010, 3 pages.
International Application No. PCT/US2009/038414; Written Opinion, mailed May 29, 2010, 5 pages.
EP Application No. 09724674.8; Amendment, filed Dec. 13, 2010, 5 pages.
Extended European Search Report; Dated: May 7, 2013; European Application No. 09724674.8; 11 pages.

* cited by examiner

TRIPLE LUMEN CATHETER

RELATED APPLICATION

This application claims priority to U.S. Provisional Application No. 61/039,655, filed on Mar. 26, 2008, which is herein incorporated by reference.

FIELD OF THE INVENTION

This invention relates to catheters that are inserted into a patient's body for diagnostic or therapeutic purposes. The invention specially relates to multiple-lumen intravenous catheters that are suitable, as one of the intended applications, for pressurized injection of diagnostic and therapeutic agents.

BACKGROUND OF THE INVENTION

Infusion of drugs, medications, or other diagnostic and therapeutic agents into the vascular system of a patient is a task routinely required by modern medicine. Placement of central venous access devices is a common occurrence in hospitals for these purposes. They are essentially used to give intra venous medications, obtain venous samples of blood and obtain measurements of central venous pressure. Three of the most commonly used devices are the Totally Implantable Venous Access System (TIVAS), the Peripherally Inserted Central Catheter (PICC), and the Central Venous Catheter. A TIVAS usually consists of a reservoir compartment (the portal) that has a silicone bubble for needle insertion (the septum), with an attached plastic tube (the catheter). The device is surgically inserted under the skin in the upper chest or in the arm, and the catheter is inserted into a vein. A PICC is inserted in a peripheral vein, such as the cephalic vein, basilic vein, or brachial vein and then advanced through increasingly larger veins, toward the heart until the tip rests in the distal superior vena cava or cavo-atrial junction. The proximal end of the PICC remains outside of the body. A central venous catheter is also referred to as a chest catheter or a Hickman line. The distal end of the catheter enters the jugular vein and advances into the superior vena cava. The proximal end of the catheter tunnels under the skin and exits on the chest wall. When inserting a PICC or Hickman line, a stainless steel wire (guide wire) is used to guide the flexible catheter through the vasculature to its intended site of placement.

Angiography is a medical imaging technique in which an X-ray picture is taken to visualize the inner opening of blood filled structures, including arteries, veins and the heart chambers. A computed tomography (CT) technique can also be used to generate detailed three dimensional images. Because blood has the same radiodensity as the surrounding tissues, a radio-contrast agent is added to the blood to make angiography visualization possible. A large amount of contrast agent infused in a short period of time is usually necessary for successfully obtaining images with good contrast. Power injection equipment is routinely employed with central venous access catheters to achieve the required rate of delivery. Clinical injection rates can go as high as 5 mL/sec. Other medical procedures, such as in the treatment of dehydration and sepsis, may also require infusion of large amounts of fluid through a central venous line.

PICC insertion is less traumatic compared to a central venous catheter. Multiple-lumen catheters have the distinct advantage of enabling multiple diagnostic and therapeutic access through a single placement procedure. Some patients undergoing imaging examinations may already have a PICC placed for other purposes. Insertion of a traditional central venous catheter solely for the purpose of imaging examination can be traumatic for the patients and cumbersome for the medical staff.

Existing multiple-lumen PICCs may be used for power injection of diagnostic and therapeutic agents. The internal lumens of existing multiple-lumen PICC are generally configured as represented in FIGS. 1A and 1B. In the PICC depicted in FIG. 1A, the lumens 110 are formed by three septa 120 arranged radially, extending from the outer wall 130 of the catheter to the center of the catheter. Angular corners are formed at the intersection between the septa 120, and between each of the septum 120 and the outer wall 130 of the catheter. During the placement of a PICC, one of the lumens must be used to thread the guide wire. The angular corners in the catheter lumens have a tendency to catch the guide wire, and make PICC placement difficult. The radially arranged lumens 110 in FIG. 1A also do not perform well under pressure. The angular corners of the lumens are prone to rupture under pressure.

FIG. 1B depicts the cross section of another example of a multiple-lumen catheter having three lumens with circular cross sections. A larger lumen 140 is formed on one side of the catheter, with two smaller lumens 150 on the other side. The larger lumen 140, which lacks any angular corners, is naturally suited to be used with the guide wire for advancement of the PICC. However, the diameter of the larger lumen 140 is relatively small compared to the usable space within the body of the catheter. As can be seen when viewing the FIG. 1B embodiment, the use of space is not very efficient. The small diameter of the larger lumen 140 also restricts the maximum flow rate achievable through this lumen. High pressure resulting from the required flow rate for power injection would reach unsafe levels that may cause catheter rupture. Further, the structural weak point of the larger lumen is its outer wall 160. In the event of a catheter rupture, the outer wall 160 of the larger lumen 140 is the likely place to breach. Fluid in the larger lumen 140 may escape into the surrounding tissue, and cause complications. For the foregoing reasons, a PICC with the FIG. 1B configuration is generally not suitable for power injection.

To increase the pressure rating for the multiple-lumen PICCs with the afore-mentioned existing lumen configurations, a practitioner may have to increase the diameter of the inner lumen by increasing the overall diameter of the PICC. The multiple-lumen PICCs that are currently available on the market are generally of large diameters, typically 6 Fr or larger. The relatively large size of the existing multiple-lumen PICC is not an ideal solution, because it would make PICC placement more difficult and diminish the advantage of PICCs over central venous lines. Accordingly, it would be desirable to have a multiple-lumen PICC capable of use for power injection of diagnostic and therapeutic agents, while still having a traditional outer dimension and being configured (without small angular corners) for easy insertion over a guide wire. Particularly it would be desirable to have a triple lumen power injection PICC with an outer diameter of 5 Fr or less. Additionally, it would be desirable to have a multiple-lumen PICC that is fail safe. In case of a lumen rupture when the catheter is used under pressure, the integrity of the exterior wall is retained.

SUMMARY OF THE INVENTION

The present invention presents a multi-lumen intravenous catheter comprising an elongated body portion having an outer wall extending longitudinally between proximal and distal ends, wherein two septa extend longitudinally through the elongated body portion, the septa and the outer wall define a central lumen and two side lumens, the central lumen has a generally oblong shape in cross section and is positioned between the two side lumens, and each of the septa are configured to flex when the central lumen is under pressure, whereby a cross sectional area of the central lumen resultantly increases to increase flow capacity through the central lumen; and a plurality of extension tubes, each having a first end and a second end, extending generally longitudinally away from the proximal end of the body portion, wherein the first ends of the extension tubes connect to the proximal end of the body portion, the central lumen and the two side lumens each form a fluid tight connection to a respective extension tube.

The present invention multi-lumen catheter may further comprise a plurality of connectors, wherein a connector is located at a second end of each of the extension tubes.

In one aspect of the present invention, the central lumen has a rounded top and bottom inner surface.

In one embodiment of the present invention, the central lumen has a generally stadium shape.

In another embodiment of the present invention, the central lumen having generally concave side surfaces and rounded top and bottom surfaces at normal atmospheric pressure, and generally convex side surfaces when under pressure.

In one embodiment of the present invention, a radius of curvature of an inner surface of each of the side lumens is in all locations equal to or greater than a radius of curvature of an outer wall of a guide wire used for insertion of the multi-lumen catheter.

In one embodiment of the present invention, a minimal thickness of the outer wall that bounds the central lumen maybe larger than a thickness of each of the septa. The outer wall is more rupture resistant than either of the septa. Each of the septa is configured to have less mechanical strength under catheter pressure than the outer wall, whereby catheter rupture will occur in one or both of the septa prior to in the outer wall. Each of the septa is configured to fail under catheter pressure before failure of the outer wall.

In one embodiment of the present invention, the sum of the cross sectional areas of the two side lumens is less than the cross sectional area of the central lumen. In another embodiment of the present invention, the sum of the cross sectional areas of the two side lumens does not equal the cross sectional area of the central lumen.

In one embodiment of the present invention, the side lumen is of generally "D" shape. In another embodiment of the present invention, the side lumen is of generally "C" shape. In yet another embodiment of the present invention, the side lumen is of generally circular shape. In a further embodiment of the present invention, the side lumen is of generally elliptical shape.

The present invention also provides a multi-lumen intravenous catheter comprising an elongated body portion including an outer wall extending longitudinally along and forming the elongated body portion between proximal and distal ends, and two septa extending longitudinally along, through, and forming the elongated body portion, wherein the two septa and the outer wall define a central lumen and two side lumens, the central lumen has an inner surface defining a generally stadium shape of the central lumen; and a radius of curvature of the inner surface of the central lumen is, in all locations, equal to or greater than a radius of curvature of an outer surface of a guide wire used for insertion of the multi-lumen catheter.

Additionally, the present invention also provides a multi-lumen intravenous catheter comprising an elongated body portion including an outer wall extending longitudinally along and forming the elongated body portion between proximal and distal ends, and two septa extending longitudinally along, through, and forming the elongated body portion, wherein the two septa and the outer wall define a central lumen and two side lumens, and each of the septa is configured to fail under catheter pressure before failure of the outer wall.

The present invention further provides a multi-lumen intravenous catheter comprising an elongated body portion including an outer wall extending longitudinally along and forming the elongated body portion between proximal and distal ends, and two septa extending longitudinally along, through, and forming the elongated body portion, wherein the two septa and the outer wall define a central lumen and two side lumens, and each of the septa is configured to have less mechanical strength under catheter pressure than the outer wall, whereby catheter rupture will occur in one or both of the septa prior to in the outer wall.

The present invention also provides a multi-lumen intravenous catheter comprising an elongated body portion including an outer wall extending longitudinally along and forming the elongated body portion between proximal and distal ends, and two flexible septa extending longitudinally along, through, and forming the elongated body portion, wherein the two septa and the outer wall define a central lumen and two side lumens, and the central lumen having generally concave side surfaces and rounded top and bottom surfaces at normal atmospheric pressure, and generally convex side surfaces when under pressure.

Finally, The present invention also provides a multi-lumen intravenous catheter comprising an elongated body portion including an outer wall extending longitudinally along and forming the elongated body portion between proximal and distal ends, and at least two septa extending longitudinally along, through, and forming the elongated body portion, wherein the at least two septa and the outer wall define a central lumen and at least two side lumens, wherein the central lumen is located essentially at the center of the catheter body, and at least one of the side lumen is located on a first side of the central lumen and at least one side lumen is located on a second side of the central lumen, septa are configured to flex when the central lumen is under pressure, whereby a cross sectional area of the central lumen resultantly increases to increase flow capacity through the central lumen.

DETAILED DESCRIPTION OF THE INVENTION

The advantages of the present invention will be apparent to those skilled in the art from the following specification.

Accordingly, it will be recognized by those skilled in the art that changes or modifications may be made to the below-described embodiments without departing from the broad inventive concepts of the invention. It should therefore be understood that this invention is not limited to the particular embodiments described herein, but is intended to include all changes and modifications that are within the scope and spirit of the invention. The words "proximal" and "distal" refer to directions away from and closer to the insertion tip, respectively, of a catheter of the present invention.

Figure 2:
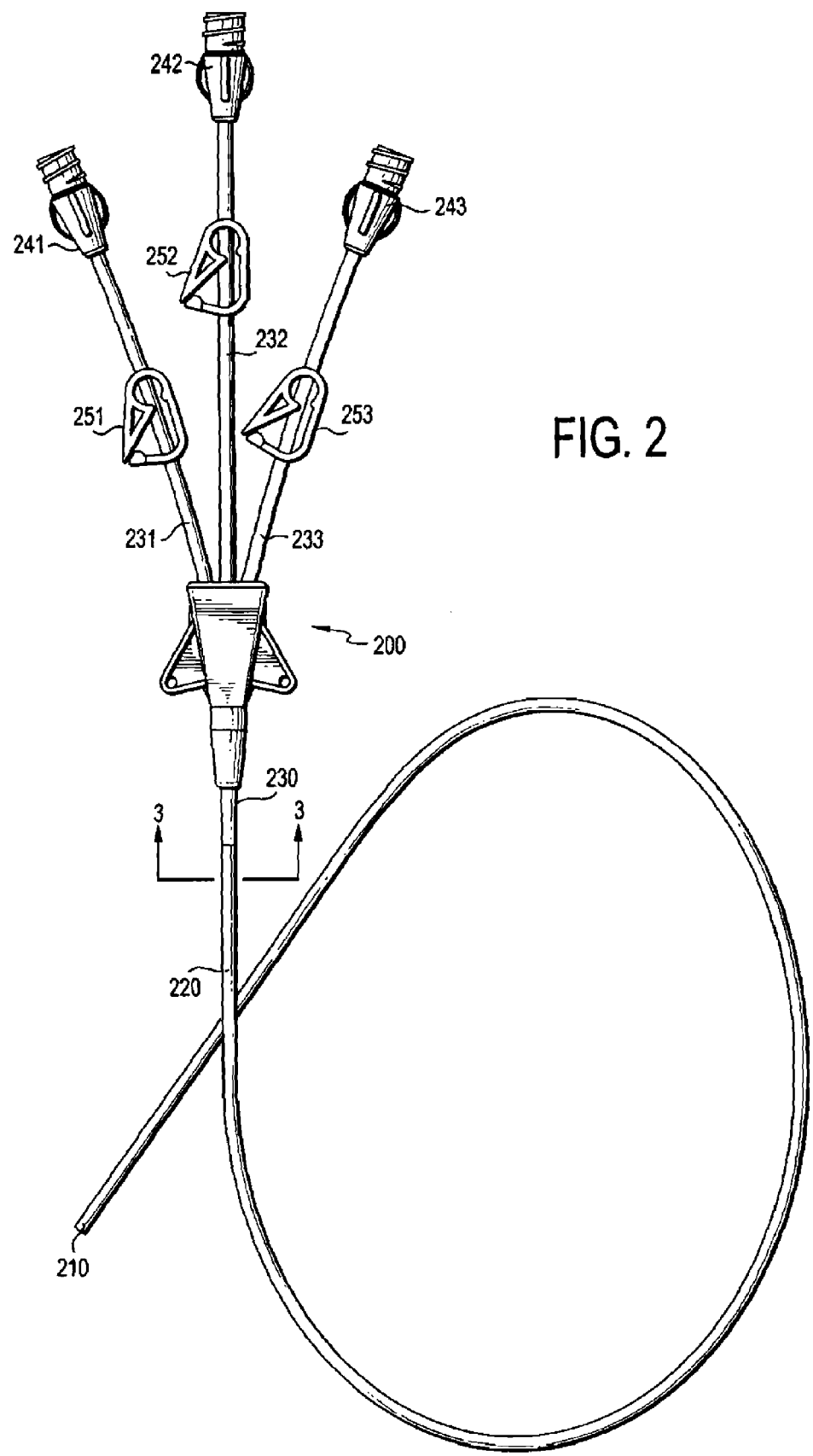
FIG. 2 is a diagrammatic side view of one embodiment of a multiple-lumen catheter.

FIG. 2 depicts a representative multiple-lumen catheter 200 employing the present invention lumen configuration. The catheter comprises an elongated body portion 220. In the distal end, the body portion 220 connects to a tip structure 210. The internal space of the body portion 220 is divided into several lumens. Each of the lumens has an opening in the tip structure 210. In the embodiment shown in FIG. 2, each of the lumens opens at the same point of the tip structure 210. In other embodiments of the present invention, openings of each of the lumens may be placed at different locations along the tip structure 210, thereby minimizing mixing and the possibility of adverse reactions when incompatible drugs or therapeutic agents are delivered at the same time through separate lumens of the catheter. Other tip structures well know in the art can also be used with the present invention. The proximal end 230 of the body portion 220 of the catheter connects to a plurality of extension tubes 231 232 233. Each of the internal lumen forms a fluid tight connection to an extension tube 231 232 233. In some embodiments of the present invention more than one lumen can be connected to a single extension tube. Each of the extension tubes 231 232 233 further may connect to a connector of a type commonly used in medical applications 241 242 243, such as Luer-Lock type connecters, which provides easy linkage to other medical instruments or devices. Connectors for the present invention multiple-lumen catheter may be manufactured separately from the catheter, and are attached during insertion of the catheter assembly. Clamps 251 252 253 may be placed on the extension tubes to stop fluid flow when the catheter is not in use.

The pressure generated by injection of fluid though a rigid tube can be described by Poiseuille's Law, which states that: $Q=(\rho^4 \Delta P)/(\eta 8L)$. The rate of flow through a rigid tube (Q) is proportional to the fourth power of the radius of the tube (r) and the difference in pressure at the two ends of the tube ($\Delta P$), and is inversely related to the viscosity of the fluid ($\eta$) and the length of the tube (L). The body portion 220 of catheter is usually made of material that is flexible, such as silicone or polyurethane or other tissue compatible polymers. Although not directly applicable, Poiseuille's Law provides important guidance to approximate fluid flow characteristics within a multiple-lumen catheter where the walls may flex and expand slightly under pressure.

Figure 1A:
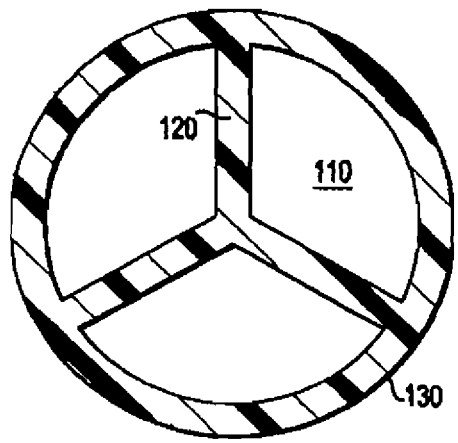
FIG. 1A and FIG. 1B are schematic cross section views of existing, prior art triple lumen catheters.
Figure 1B:
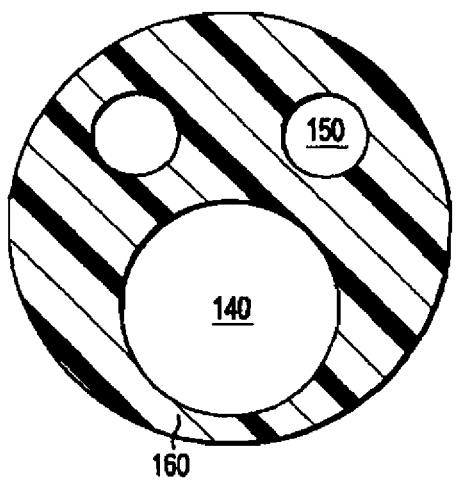
Figure 3:
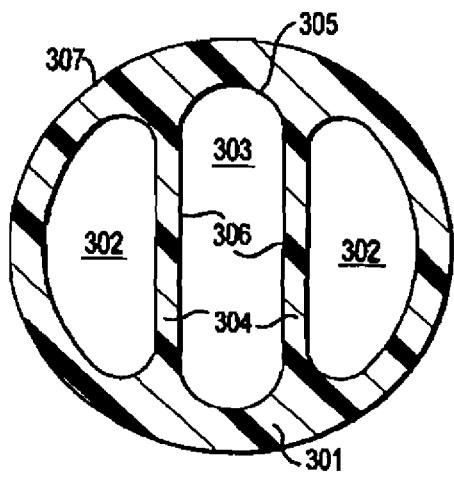
FIG. 3 is a schematic cross section view of the body portion of one embodiment of the present invention multiple lumen catheter.

FIG. 3 shows a cross section view of the catheter body of one embodiment of the present invention. Two septa 304 divide the internal space of the body portion 220 into three lumens 302 303. The lumens are arranged in a side-by-side configuration. The central lumen 303 is located essentially in the center of the catheter body, and the two side lumens 302 are located on each side of the central lumen 303. The central lumen 303 is defined by the two septa 304 and the outer wall 301 of the catheter, and is positioned between the two side lumens 302. The central lumen 303 has a generally stadium shape in cross section. In the embodiment shown in FIG. 3, the central lumen 303 is formed by septa with essentially planar side surfaces 306, and rounded top and bottom surfaces 305. In other embodiments, the central lumen 303 may have a cross section of an elongated circle, an ellipse, or other shapes that efficiently utilize the internal space of the catheter. In the embodiment shown in FIG. 3, the side lumens 302 have a crescent or "D" shape in cross section. In other embodiments, the side lumens 302 can have circular, elliptical, "C" shaped, or other suitable cross sections. The shape of the cross sections of the central lumen 303 and side lumens 302 is chosen so that it provides optimal utilization of the internal space of the body portion 220 of the catheter. The rounded top and bottom surfaces 305 of the central lumen 303 and the outer surface 307 of the catheter body portion 220 form the outer wall 301 of the catheter body portion 220.

The rounded top and bottom interior surfaces 305 of the central lumen 303 connect smoothly to the side surfaces 306. The inner surface 305 306 of the central lumen 303 is free from any sharp corners. The smooth inner surface 305 306 of the central lumen 303 is optimal for catheter placement along a guide wire. The radius of curvature of the inner surface 305 is chosen to minimize the possibility that any corner within the central lumen 303 can catch the guide wire and hinder the advance of the catheter 200 along the guide wire. For example, if a guide wire of 0.018 in. diameter is intended, the radius of curvature for any corner in the central lumen 303 would preferably be equal to or larger than 0.009 in. Accordingly, in one aspect of the invention, the radius of curvature within the central lumen 303 (and/or within the side lumens 302) is in all locations (i.e., at all points along the inner wall of the central lumen 303 and/or the side lumens 302) equal to or greater than the radius of curvature of the outer wall (or outer perimeter surface) of an associated guide wire.

Figure 4:
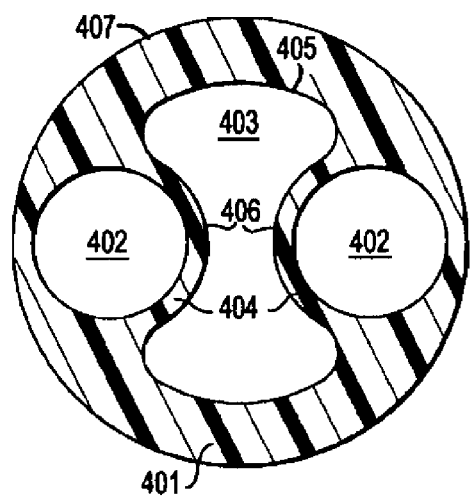
FIG. 4 is a schematic cross section view of the body portion of a second embodiment of the present invention multiple lumen catheter.

FIG. 4 shows a cross section view of a second embodiment of the present invention. In this particular embodiment, the two side lumens 402 are of a generally circular shape. And the central lumen 403 is of a "dog bone" shape. The top and bottom interior surfaces 405 of the central lumen of the embodiment shown in FIG. 4 connect smoothly to the side surfaces 406. The entire interior surface 405 406 of the central lumen 403 is free of sharp corners. The septa 404 between the two side lumens 402 and the central lumen 403 protrude into the central lumen 403 at normal atmospheric pressure, i.e., the septa 404 are of generally concave shape. When under pressure, such as during a power injection procedure, the septa 404 are capable of deforming and may be pushed outward. The side lumens 402, as a consequence, may have reduced size under pressure. Thus, the septa 404 may adopt a convex shape under pressure.

The potential to deform and expand the diameter of the central lumen 403 provides the present invention excellent flow performance when the overall exterior diameter is of a small size. The outer wall 401 of the catheter can be made thicker at the top and bottom of the central lumen than the septa 404. This configuration would help to provide stronger mechanical strength to the exterior wall of the catheter body 220.

Figure 5:
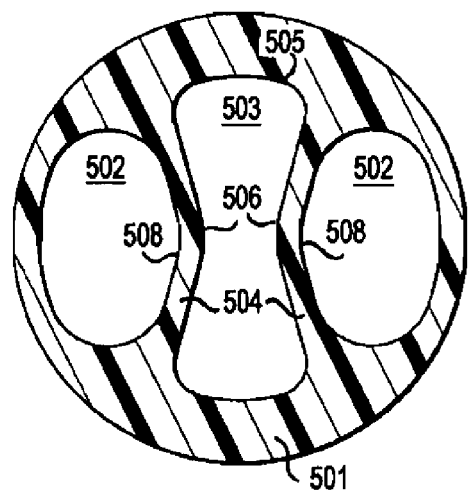
FIG. 5 is a schematic cross section view of the body portion of a third embodiment of the present invention multiple lumen catheter.

FIG. 5 shows a cross section view of a catheter body of a third embodiment of the present invention. In this particular embodiment, the central lumen 503 is of an "hour glass" shape. The two side lumens 502 are of irregular elliptical shape having interior surfaces 508 following the general shape of the side surfaces 506 of the central lumen 506. Similar to the embodiment shown in FIG. 4, the septa 504 between the two side lumens 502 and the central lumen 503 protrude into the central lumen 503 under normal atmospheric pressure, i.e., the septa 504 are of generally concave shape. When under pressure, such as during power injection procedure, the septa 504 are capable of deforming and may be pushed outward. Thus, the septa 504 would adopt a convex shape under pressure. Similarly, the outer wall 501 of the catheter can be made thicker at the top and bottom of the central lumen 503 than the septa 504. This configuration would help to provide stronger mechanical strength to the exterior wall of the catheter body 220.

Figure 6:
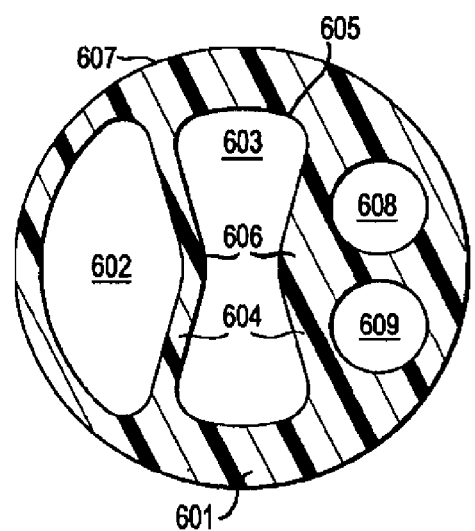
FIG. 6 is a schematic cross section view of the body portion of a fourth embodiment of the present invention multiple lumen catheter.

FIG. 6 shows a cross section view of the catheter body of a fourth embodiment of the present invention. In this particular embodiment, instead of one side lumen on one side of the central lumen 603, two smaller side lumens 608 609 are formed. This lumen configuration can be adapted to all embodiments of the present invention, which include, but are not limited to, the embodiments disclosed in FIGS. 3, 4, and 5.

For the lumen configurations shown in FIGS. 4, 5, and 6, a guide wire is preferably traversed through one of the respective side lumens 402 502 602 when used to advance the catheter. The radius of curvature within the side lumen 402 502 602 is in all locations (i.e., at all points along the inner wall of the side lumen 402 502 602) equal to or greater than the radius of curvature of the outer wall (or outer perimeter surface) of an associated guide wire.

The central lumen 303 403 503 603 of the present invention, has a large cross section (or cross-sectional area) relative to the available space (or cross-sectional area) within the body portion 220 of the catheter. Because the flow rate is proportional to the fourth power of the radius of a tube, even a small increase in the cross section of the central lumen 303 403 503 603 greatly increases the flow rate achievable though the tube when all other parameters are constant. The present invention optimizes space utilization within the body portion 220 of the catheter, allowing the body portion 220 to have a relatively thick outer wall 301 401 501 601. This increases the mechanical strength of the body portion 220, and in turn allows a higher pressure rating for the catheter 200. When the catheter 200 is under pressure, each of the septa 304 404 504 604 may flex outward, resultantly increasing the cross section of the central lumen 303 403 503 603, and thereby further facilitating fluid flow.

One shortcoming of existing multiple lumen catheter designs is that the exterior wall of the respective catheter tends to rupture first (relative to other catheter walls) when under pressure. In one aspect of the invention, the septa 304 404 504 604 of the present invention are designed to have less mechanical strength than the outer wall 301 401 501 601 of the catheter body portion 220. In another aspect, the septa 304 404 504 604 are of a thickness less than the minimal thickness of the outer wall 301 401 501 601. In still another aspect, the rupture characteristics of the septa 304 404 504 604 and the outer wall 301 401 501 601 are optimized by modifying both the thickness and the shape. This provides a fail-safe mechanism. In the event of catheter malfunction, such as a blockage, one or both of the septa 304 404 504 604 would be first to rupture (relative to the outer wall 301 401 501 601). When a septum 304 404 504 604 breach occurs, the fluid within the central lumen 303 403 503 603 would therefore leak into a side lumen 302 402 502 602 608 609. Accordingly, the integrity of the body portion 220 of the catheter 200 is retained. This configuration effectively protects against extravastation of the fluid within the central lumen 303 403 503 603 in the event of a septa 304 404 504 604 breach.

The configuration of the present invention central lumen 303 403 503 603 provides high flow rate and fail safe protection under pressure. It is, therefore, suited for power injection of diagnostic or therapeutic agents. The catheter of the present invention can be safely used at a flow rate of 5 cc/sec at 300 psi. The configuration of the lumens also provides added benefits such as kink resistance and flexibility.

The lumens of the present invention catheter are intended to be used independently to deliver drugs, therapeutic or diagnostic agents. The dimensions of the lumens are not necessarily constrained in relation to one another. The cross sectional area of the central lumen 303 403 503 603 may or may not be equal to the sum of the cross sectional areas of respective side lumens 302 402 502 602 608 609. In one embodiment of the present invention, the sum of the cross sectional areas of respective side lumens 302 402 502 602 608 609 is greater than the cross sectional area of respective central lumen 303 403 503 603. In another embodiment, the sum of the cross sectional areas of respective side lumens 302 402 502 602 is less than the cross sectional area of respective central lumen 303 403 503 603.

The present invention catheter can be manufactured to various sizes suitable for PICC applications. The unique lumen configuration of the present invention makes it possible to manufacture a triple lumen PICC with small outer diameters such as French size 5 or 6. The catheters of the present invention can be made from existing thermal plastics presently used for intravenous catheters, such as silicone and polyurethane or other tissue compatible polymers. The body portion of the catheter of the present invention can be manufactured using existing molding or extrusion manufacturing processes. Placement of the catheters of the present invention also does not require any special modification to present medical procedures.

I claim:

1. A multi-lumen intravenous catheter comprising:
   an elongated body portion having an outer wall extending longitudinally between a proximal end and a distal end wherein:
      two septa extend longitudinally through the elongated body portion, wherein the two septa and the outer wall define a central lumen and two side lumens,
      the central lumen has a generally oblong shape in cross section and is positioned between the two side lumens, and
      each of the two septa are configured to flex when the central lumen is under pressure,
      whereby a cross sectional area of the central lumen resultantly increases to increase flow capacity through the central lumen;
   a plurality of extension tubes, each extension tube having a first end and a second end, extending generally longitudinally away from the proximal end of the body portion, wherein the first end of the extension tube connect to the proximal end of the body portion, the central lumen and the two side lumens each form a fluid tight connection to a respective extension tube; and
   wherein a radius of curvature of an inner surface of each of the side lumens is in all locations equal to or greater than a radius of curvature of an outer wall of a guide wire used for insertion of the multi-lumen catheter.

2. The multi-lumen catheter of claim 1, further comprising:
   a plurality of connectors, wherein a connector is located at a second end of each of the extension tubes.

3. The multi-lumen catheter of claim 1, wherein the central lumen has a rounded top and a bottom inner surface.

4. The multi-lumen catheter of claim 1, wherein the central lumen has a generally stadium shape.

5. The multi-lumen catheter of claim 1, wherein the central lumen has generally concave side surfaces and a rounded top surface and a rounded bottom surfaces at normal atmospheric pressure, and generally convex side surfaces when under pressure.

6. The multi-lumen catheter of claim 1, wherein a minimal thickness of the outer wall of the elongated body portion is larger than a thickness of each of the two septa.

7. The multi-lumen catheter of claim 1, wherein the outer wall of the elongated body portion is more rupture resistant than either of the two septa.

8. The multi-lumen catheter of claim 1, wherein each of the two septa is configured to have less mechanical strength under catheter pressure than the outer wall of the elongated body portion, whereby catheter rupture will occur in one or both of the two septa prior to in the outer wall.

9. The multi-lumen catheter of claim 1, wherein each of the two septa is configured to fail under catheter pressure before failure of the outer wall of the elongated body portion.

10. The multi-lumen catheter of claim 1, wherein the sum of the cross sectional areas of the two side lumens is less than the cross sectional area of the central lumen.

11. The multi-lumen catheter of claim 1, wherein the sum of the cross sectional areas of the two side lumens does not equal the cross sectional area of the central lumen.

12. The multi-lumen catheter of claim 1, wherein the side lumen is of generally "D" shape.

13. The multi-lumen catheter of claim 1, wherein the side lumen is of generally "C" shape.

14. The multi-lumen catheter of claim 1, wherein the side lumen is of generally circular shape.

15. The multi-lumen catheter of claim 1, wherein the side lumen is of generally elliptical shape.

16. A multi-lumen intravenous catheter comprising an elongated body portion including:
   an outer wall extending longitudinally along and forming the elongated body portion between a proximal end and a distal end; and
   two septa extending longitudinally along and through the elongated body portion, wherein:
      the two septa and the outer wall define a central lumen and two side lumens;
      the central lumen has an inner surface defining a generally stadium shape of the central lumen; and
      a radius of curvature of the inner surface of the central lumen is, in all locations, equal to or greater than a radius of curvature of an outer surface of a guide wire used for insertion of the multi-lumen catheter.

\* \* \* \* \*